United States Patent [19]

Meares et al.

[11] Patent Number: 5,958,374
[45] Date of Patent: Sep. 28, 1999

[54] METHOD FOR PREPARING RADIONUCLIDE-LABELED CHELATING AGENT-LIGAND COMPLEXES

[75] Inventors: Claude F. Meares; Min Li, both of Davis; Sally J. DeNardo, El Macero, all of Calif.

[73] Assignee: The Regents of the University of California, Oakland, Calif.

[21] Appl. No.: 08/767,702

[22] Filed: Dec. 17, 1996

Related U.S. Application Data

[63] Continuation of application No. 08/218,591, Mar. 28, 1994, abandoned.

[51] Int. Cl.$^6$ .............................. A61K 51/00; C07F 5/00
[52] U.S. Cl. ...................... 424/1.65; 424/1.69; 424/1.49; 424/1.53; 424/1.11; 534/10
[58] Field of Search .................................. 424/1.53, 1.65, 424/1.69, 1.49, 1.11; 534/10, 11, 13, 14

[56] References Cited

U.S. PATENT DOCUMENTS

| | | | |
|---|---|---|---|
| 4,885,363 | 12/1989 | Tweedle et al. | 540/465 |
| 5,006,643 | 4/1991 | Fazio et al. | |
| 5,217,704 | 6/1993 | Johnson et al. | |
| 5,284,644 | 2/1994 | Kruper, Jr. et al. | |
| 5,435,990 | 7/1995 | Cheng et al. | 424/1.53 |
| 5,514,363 | 5/1996 | Shochat et al. | 424/1.49 |

FOREIGN PATENT DOCUMENTS

WO 89/12631  12/1989  WIPO.

OTHER PUBLICATIONS

Moi, M.K., et al., "Copper chelates as probes of biological systems: Stable copper complexes with a macrocyclic bifunctional chelating agent" *Anal. Biochem.* (1985) 148:249–253.

Moi, M.K., et al., "The peptide way to macrocyclic bifunctional chelating agents: Synthesis of 2–(p–nitrobenzyl)–1,4,7,10–tetraazacyclododecane–N,N',N",N"'–tetraacetic acid and study of its yttrium(III) complex" *J. Am. Chem. Soc.* (1988) 110:6266–6267.

Cox, J.P.L., et al., "Synthesis of C– and N–functionalised derivatives of 1,4,7–triazacyclononane–1,4,7–triyltriacetic acid (NOTA), 1,4,7,10–tetra–azacyclododecane–1,4,7,10–tetrayltetra–acetic acid (DOTA), and diethylenetri-aminepenta–acetic acid (DPTA): Bifunctional complexing agents for the derivatisation of antibodies" *J. Chem. Soc. Perkin Trans. 1* (1990) pp. 2567–2576.

Parker, D., "Tumour targeting with radiolabelled macrocycle–antibody conjugates" *Chem. Soc. Rev.* (1990) 19:271–291.

Meares, C.F., et al., "Macrocyclic chelates of radiometals for diagnosis and therapy" *Brit. J. Cancer* (1990) 10:21–26.

Gansow, O.A., "Newer approaches to the radiolabelling of monoclonal antibodies by use of metal chelates" *Nucl. Med. Biol.* (1991) 18:369–381.

Li, M., et al., "Synthesis, metal chelate stability studies, and enzyme digestion of a peptide–linked DOTA derivative and its corresponding radiolabeled immunoconjugates" *Bioconjugate Chem.* (1993) 4:275–283.

Deshpande, S.V., et al., "Yttrium–90–labeled monoclonal antibody for therapy: Labelling by a new macrocyclic bifunctional chelating agent" *J. Nucl. Med.,* (1990) 31:473–479.

Kasprzyk, S.P., et al., "Kinetics of interaction of metal ions with two tetraaza tetraacetate macrocycles" *Inorg. Chem.* (1982) 21:3349–3352.

Kodama, M., et al., "Thermodynamic and kinetic studies of lanthanide complexes of 1,4,7,10,13–pentaazacyclopentadecane–N,N', N", N"', N""–pentaacetic acid and 1,4,7,10,13,16–hexaazacyclo octadecane–N,N',N",N"', N"", N""'–hexaacetic acid" *Inorg. Chem.* (1991) 30:1270–1273.

Wang, X., et al., "A kinetic investigation of lanthanide DOTA chelates. Stability and rates of formation and of dissociation of a macrocyclic gadolinium(III) polyaza polycarboxylic MRI contrast agent" *Inorg. Chem.* (1992) 31:1095–1099.

Fritzberg, A.R., et al., "Specific and stable labeling of antibodies with technetium–99m with a diamide dithiolate chelating agent" *Proc. Natl. Acad. Sci. USA* (1988) 85:4025–4029.

Franz, J., et al., "The production of $^{99m}$Tc–labeled conjugated antibodies using a cyclam–based bifunctional chelating agent" *Nucl. Med. Biol.* (1987) 14:569–572.

Linder, K.E., et al., "Technetium labeling of monoclonal antibodies with functionalized BATOs. 1. TcCl(DMG)$_3$PITC" *Bioconjugate Chem.* (1991) 2:160–170.

Schlom, J., et al., "Monoclonal antibody–based therapy of a human tumor xenograft with a $^{177}$Lutetium–labeled immunoconjugate" *Cancer Res.* (1991) 51:2889–2896.

Kosmas, C., et al., "Development of humoral immune responses against a macrocyclic chelating agent (DOTA) in cancer patients receiving radioimmunoconjugates for imaging and therapy", *Cancer Res.* (1992) 52:904–911.

Wessels, B.W., et al., "Radionuclide selection and model absorbed dose calculations for radiolabeled tumor associated antibodies" *Med. Phys.* (1984) 11:638–645.

Fell, H.P., et al., "Chimeric L6 anti–tumor antibody", *J. Biol. Chem.* (1992) 267:15552–15558.

(List continued on next page.)

Primary Examiner—Jose' G. Dees
Assistant Examiner—Michael G. Hartley
Attorney, Agent, or Firm—Morrison & Foerster LLP

[57] ABSTRACT

Radionuclide-labeled chelating agent-ligand complexes that are useful in medical diagnosis or therapy are prepared by reacting a radionuclide, such as $^{90}$Y or $^{111}$In, with a polyfunctional chelating agent to form a radionuclide chelate that is electrically neutral; purifying the chelate by anion exchange chromatography; and reacting the purified chelate with a targeting molecule, such as a monoclonal antibody, to form the complex.

14 Claims, 2 Drawing Sheets

OTHER PUBLICATIONS

Penefsky, H.S., "A centrifuged–column procedure for the measurement of ligand binding by beef hears $F^1$" et al., *Meth. Enzymol.* (1979) 56:Part G: 527–530.

Meares, C.F., et al., "Conjugation of antibodies with bifunctional chelating agents: Isothiocyanate and bromoacetamide reagents, methods of analysis, and subsequent addition of metal ions" *Anal. Biochem.* (1984) 142:68–78.

DeNardo, S.J., et al., "Immunochemical aspects of monoclonal antibodies important for radiopharmaceutical development" *Nucl. Med. Biol.* (1986) 13:303–310.

Hellström, I., et al., "Monoclonal mouse antibodies raised against human lung carcinoma" (1986) *Cancer Res.* (1986) 46:3917–3923.

*Encyclopedia of Chemical Technology,* 4th vol. 14, 1995, pp. 737–741.

METHOD FOR PREPARING RADIONUCLIDE-LABELED CHELATING AGENT-LIGAND COMPLEXES

RELATED APPLICATIONS

This application is a continuation of U.S. Ser. No. 08/218,591, filed Mar. 28, 1994, abandoned.

REFERENCE TO GOVERNMENT SUPPORT

This invention was made in part with Government support under contract number CA16861 and CA47829 awarded by the Department of Health and Human Services and contract number DE FG03-84ER60233 awarded by the Department of Energy. The Government has certain rights in this invention.

DESCRIPTION

1. Technical Field

This invention relates to a method for preparing radionuclide-containing compounds that are useful for medical diagnosis and therapy.

2. Background Art

Macrocyclic bifunctional chelating agents have been developed to tag monoclonal antibodies (mAbs) with radiometals for in vivo diagnosis and therapy [Moi et al., 1985, Anal. Biochem., 148:249–253; Moi et al., 1988, J. Am. Chem. Soc., 110:6266–6267; Cox et al., 1990, J. Chem. Soc. Perkins Trans. 1, 2567–2576; Parker, 1990, Chem. Soc. Rev., 19:271–291; Meares et al., 1990, British J. Cancer, Suppl., 10:21–26; Gansow, 1991, Nucl. Med. Biol., 18:369–381; Li et al., 1993, Bioconjugate Chem., 4:275–283]. In particular, mAbs labeled with DOTA (1,4,7,10-tetraazacyclododecane-N,N',N'',N'''-tetraacetic acid) derivatives incorporating yttrium-90 ($^{90}$Y) and indium-111 ($^{111}$In) have shown excellent kinetic stability under physiological conditions [Moi et al., 1988; Meares et al., 1990; Li et al., 1993; Deshpande et al., 1990, J. Nucl. Med., 31:473–479]. However, the slow formation of yttrium-DOTA complexes [Kapryzyk et al., 1982, Inorg. Chem., 21:3349–3352; Kodama et al., 1991, Inorg. Chem., 30:1270–1273; Wang et al., 1992, Inorg. Chem., 31:1095–1099] presents a technical problem that can lead to low radiolabeling yields unless conditions are carefully controlled.

These chelating agent-mAb-radionuclide conjugates have been synthesized using two methods. In one, the chelating agent is first conjugated to the antibody and then the resulting conjugate is labeled with radionuclide. In the other, called "prelabeling", the chelating agent is first labeled with the radionuclide, the labeled chelating agent is purified, and the purified labeled chelating agent is conjugated to the antibody. Prelabeling has several potential advantages over the other method. In the labeling step, metal chelate formation is easier to control because there is no competition from metal binding sites on the mAb and there is no danger of denaturing the antibody during labeling. The removal of unreacted chelating agent in the purification step avoids the production of multiply labeled immunoconjugates with unfavorable biological properties. Finally, prelabeling minimizes chemical manipulation of the antibody and reduces loss of antibody activity.

Prelabeling has been used to label mAbs with $^{99}$Tc [Fritzberg et al., 1987, Proc. Natl. Acad. Sci. U.S.A., 85:4025–4029; Franz et al., 1987, Nucl. Med. Biol., 14:569–572; Linder et al., 1991, Bioconjugate Chem., 2:160–170], $^{67}$Cu [Moi et al., 1985, supra] and $^{177}$Lu [Schlom et al., 1991, Cancer Res., 51:2889–2896]. It has not heretofore been used to label mAbs with $^{90}$Y or $^{111}$In.

In these prior instances of prelabeling, the metal chelate has either not been purified prior to conjugation [Moi et al., 1985, supra] or has been purified by HPLC [Fritzberg et al., 1987; Schlom et al., 1991, supra]. It is noted that Moi et al. use anion exchange chromatography to characterize their chelate (as a divalent anion) but not to purify it. The use of HPLC is not desirable because it employs mixed aqueous/organic solvents for elutions.

DISCLOSURE OF THE INVENTION

The present invention applies the prelabeling process to $^{90}$Y and $^{111}$indium labeling and provides a prelabeling process that employs anion exchange chromatography to purify the radionuclide chelate.

Accordingly, one aspect of the invention is a method for preparing a yttrium- or indium-labeled chelating agent-ligand complex comprising:

(a) reacting a chelating agent that has a trivalent chelating group and at least one pendant linker group that is capable of covalently binding to a ligand, with yttrium-90 or indium-111 to form an electrically neutral yttrium-90 or indium-111 chelate;

(b) purifying the chelate from the reaction mixture of step (a); and (c) reacting the purified chelate of step (b) with the ligand to form said complex.

Another aspect of the invention is a method for preparing a radionuclide-labeled chelating agent-ligand complex comprising:

(a) reacting a chelating agent that has a chelating group and at least one pendant linker group that is capable of covalently binding a ligand, with a radionuclide to form a radionuclide chelate;

(b) purifying the radionuclide chelate from the reaction mixture of step (a) by anion exchange chromatography; and (c) reacting the purified radionuclide chelate of step (b) with the ligand to form said complex.

DETAILED DESCRIPTION OF THE INVENTION

A. The Novel Prelabeling Method

Figure 1:
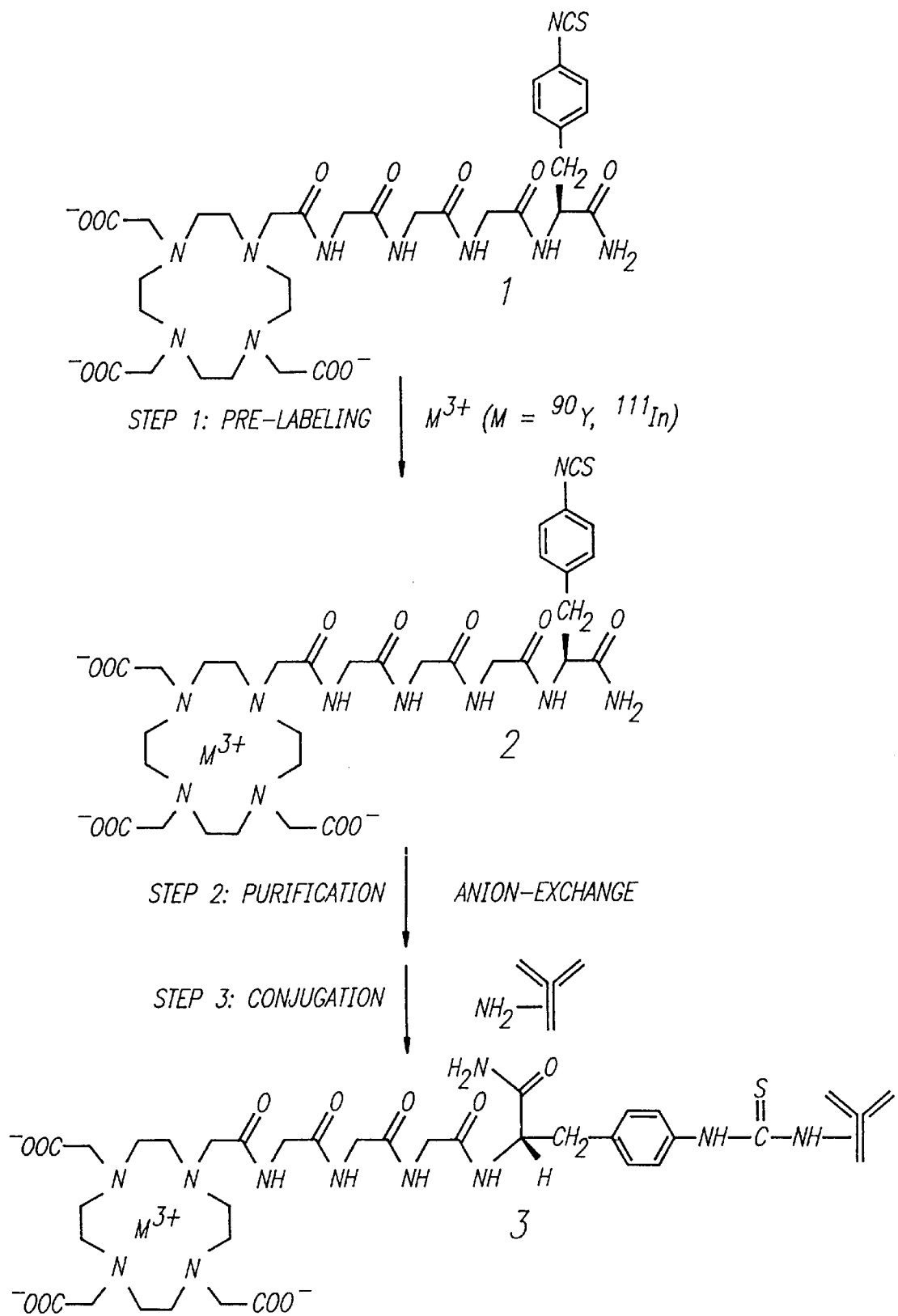
FIG. 1 is a flow chart that illustrates the synthetic route used for the preparation of radionuclide-labeled chelating ligand complexes.

Prelabeling involves three steps: (1) formation of a radiolabeled chelate (in the absence of ligand(s)), (2) purification of the radiolabeled chelate, and (3) conjugation of the purified radiolabeled chelate with ligand(s) to form a radiolabeled chelating agent-ligand complex.

The medically useful radiometals which are important for practical applications have short half-lives [Wessels et al., 1984, Med. Phys., 11:638–645] and high efficiencies of both labeling and conjugation. The prelabeling approach permits use of a large excess of chelating agent to achieve a high chelation yield quickly in step (1), but requires a rapid purification method to remove unlabeled reagent in step (2). The present invention provides an easy and efficient method for prelabeling a chelating agent (for example, a peptide-linked DOTA derivative) with a radiometal (for example, $^{90}Y$ or $^{111}In$) and subsequently conjugating it to a targeting molecule (for example, a mAb).

In the conventional labeling method, the number of radionuclide chelating moieties attached to each targeting molecule is usually >1 in order to provide enough chelating groups for a good radiolabeling yield. However, the chelating groups that actually chelate radionuclides comprise less than 5% of the total attached chelating groups on the targeting molecule. The excess chelating groups may affect the biological properties of the targeting molecule, e.g. by inducing an immune response [Kosmas et al., 1992, supra], and impure metal solutions may require large amounts of the targeting molecule.

With prelabeling, a far smaller number of chelates are attached to the targeting moiety, but practically all are radiolabeled; thus the number of modified targeting molecules is significantly reduced, and the number of multiply-modified targeting molecules is essentially zero. For example, when the targeting molecule is a mAb, the radiolabeled mAbs are fully immunoreactive and are expected to have more favorable biological properties, including reduced immunogenicity.

B. Formation of the Radiolabeled Chelate

The first step of prelabeling involves the formation of a radiolabeled-chelating agent (also referred to as a radiolabeled chelate) from a chelating agent and an appropriate radionuclide.

Synthetic methods for the preparation of chelating agents useful in the practice of the invention are known in art [see, for example Li et al., 1993, supra].

Methods for the preparation of radiolabeled chelates by reaction of a radionuclide with a chelating agent are known in the art [see, for example, Moi et al., 1985, supra]. Typically, the chelating agent is dissolved in a buffered aqueous medium and the purified radionuclide added. The pH may be selected to optimize conditions for chelate formation. For example, when chelation is achieved by acetate groups binding to the metal ion (as is the case for various acetic acid compounds), the pH may be adjusted (using, for example, aqueous tetramethylammonium acetate, to obtain of pH of about 3 to about 6, more preferably about 5) to provide a preponderance of ionized carboxylate (—COO⁻) groups, and thereby yield a chelating species which is anionic. Furthermore, the reaction mixture temperature may be adjusted, for example to 37° C. for 30 min, to accelerate the reaction (chelation). After a period of time or upon completion of reaction, an excess of an appropriate quenching agent, such as DTPA may be added. The quenching agent acts to form anionic quenching chelates with any radionuclide not yet chelated by the chelating agent. The resulting reaction mixture may then be purified by the second step of prelabeling.

The term "radionuclide", as used herein, relates to medically useful radionuclides, including, for example, positively charged ions of radiometals such as Y, In, Cu, Lu, Tc, Re, Co, Fe and the like, such as $^{90}Y$, $^{111}In$, $^{67}Cu$, $^{77}Lu$, $^{99}Tc$ and the like, preferably trivalent cations, such as $^{90}Y$ and $^{111}In$.

The term "chelating agent", as used herein, relates to polyfunctional compounds have a chelating group and at least one pendant linker group, wherein the chelating group is capable of chelating with a radionuclide, and the pendant linker group(s) is capable of covalently binding to one or more targeting molecules which may be the same or different. Chelating agents may be represented by the formula $A(L)_n$ wherein A represents the chelating moiety, L represents a pendant linking group, and n is an integer from 1 to 3, preferably 1. The pendant linker group includes one or more functional group(s) which are capable of covalently binding to targeting molecule(s).

Chelating groups capable of chelating radionuclides include macrocycles, linear, or branched moieties. Examples of macrocyclic chelating moieties include polyaza- and polyoxamacrocycles. Examples of polyazamacrocyclic moieties include those derived from compounds such at 1,4,7,10-tetraazacyclododecane-N,N',N",N'"-tetraacetic acid (herein abbreviated as DOTA); 1,4,7,10-tetraazacyclotridecane-N,N',N",N'"-tetraacetic acid (herein abbreviated as TRITA); 1,4,8,11-tetraazacyclotetradecane-N,N',N",N'"-tetraacetic acid (herein abbreviated as TETA); and 1,5,9,13-tetraazacyclohexadecane-N,N',N",N'"-tetraacetic acid (abbreviated herein abbreviated as HETA). Examples of linear or branched chelating moieties include those derived from compounds such as ethylenediaminetetraacetic acid (herein abbreviated as EDTA) and diethylenetriaminepentaacetic acid (herein abbreviated as DTPA).

Chelating moieties having carboxylic acid groups, such as DOTA, TRITA, HETA, HEXA, EDTA, and DTPA, may be derivatized to convert one or more carboxylic acid groups to amide groups.

The term "pendant linker group", as used herein, relates to moieties which are attached to the chelating group, and which have at least one functional group which is capable of covalently binding to targeting molecules. Where pendant linkers or chelating agents have a plurality of such functional groups, they may be the same or different. When the chelating moiety is macrocyclic, the pendant moiety may be attached to any annular atom. For example, when the chelating moiety is a polyazamacrocycle, the pendant group may be attached to an annular carbon atom or an annular nitrogen atom. When the pendant group is attached to an annular nitrogen atom, the compound may be referred to as an N-substituted polyazamacrocycle.

The term "functional groups capable of covalently binding to targeting molecules", as used herein, includes those functional groups which can be activated by known methods, so as to be capable of covalently binding to targeting molecule(s); for example, the formation of active esters (—C(=O)OR, wherein R is, for example, succinimidyl) from carboxylic acids, the formation of acid halides (—C(=O)X, wherein X is typically Cl or Br) from carboxylic acids.

The functional group(s) present on the pendant linker group which are capable of covalently binding to targeting molecules may be chosen according to the targeting molecule(s) to which the chelating agent will ultimately be bound. Reactive pairs of functional groups permit conjugation of the chelating agent with the targeting molecule, via the linker group, wherein one member of the pair is present on the chelating agent and the other member of the pair is present on the targeting molecule. For example, when the targeting molecule is a protein possessing a free amino (—NH₂) group, a functional group such as isothiocyanate (—NCS) present on the chelating agent permits reaction to form a joining linkage (in this case, a thiourea linkage), thereby forming a chelating agent-targeting molecule complex. Other examples of appropriate reactive pairs of functional groups include, for example, —NH₂ with —C(=O)OR (active ester) or with —C(=O)OC(=O)R (anhydride)

or with —C(=O)X (acid halide) to yield an amide linkage; —NH$_2$ with —NCO (isocyanate) to yield a urea linkage. Other reactive pairs involving —NH$_2$ include —NH$_2$ and —S(=O)$_2$X (sulfonyl halide); —NH$_2$ and —C(=NR)OR (imidate ester); and —NH$_2$ and —OC(=O)X (haloformate). Examples of reactive pairs of functional groups include —SH and —C(=O)CH$_2$X (haloacetyl) to yield a —SCH$_2$C(=O)— linkage; —SH and -alkyl-X (alkyl halide) or —SH and —S(=O)O-alkyl (alkyl sulfonate) to yield a thioether; and —SH and —SH (sulfhydryl) to yield a —SS— (disulfide) linkage.

Li et al. [Li et al., 1993, supra] have shown that the introduction of a cleavable linker between the chelate and the mAb results in a reduction of accumulated radioactivity in the liver [Li et al., 1993, supra]. Preferably, radionuclide-labeled chelating agent-ligand complexes will be cleavable in vivo. This may be achieved by introducing a cleavable linkage within the pendant group, wherein the cleavable linkage is cleaved in vivo, for example, by enzymatic action within the liver. Examples of such cleavable linkages include peptide, disulfide, and ester linkages.

Examples of pendant linker groups include peptide-based linkers, such as polypeptide groups which have been derivatized to possess at least one functional group capable of covalently binding to targeting molecule(s). The number of peptide linkages present in the pendant linker group may be varied to optimize radionuclide chelation, conjugation with targeting molecule(s), in vivo cleavability, or other factors. Examples of suitable pendant linker groups include —CH$_2$—C(=O) (AA)$_m$(AA-FG), herein denoted as substituted acetyls, wherein the —CH$_2$—C(=O)— fragment may be derived from an acetate moiety, AA represents an amino acid diradical, more preferably the glycine diradical —NH—CH$_2$—C(=O)—, and m is an integer, preferably between 1 and 10, more preferably between 3 and 7, most preferably 3. AA-FG represents an amino acid N-radical (that is, the free bond is situated on the amino group of the amino acid) which has been derivatized to possess a functional group (FG) capable of covalently binding to targeting molecule(s). Preferably, the carboxylic acid group of the amino acid of AA-FG has been derivatized, for example, to form an amide. Examples of AA-FG radicals include p-isothioscyanato-phenylalanine-N-yl amide (—NHCH[C(=O)NH$_2$][CH$_2$—(p-NCS—C$_6$H$_4$)] denoted herein as p-NCS-Phe-amide, or p-NCS-L-Phe-amide). Examples of pendant groups include —CH$_2$—C(=O)(Gly)$_m$(p-NCS-Phe-amide), denoted herein as Gly$_m$(p-NCS-Phe-amide) acetyl. Further examples of pendant linker groups include disulfides, such as alkyl disulfides including —CH$_2$—C(=O)—(CH$_2$)$_p$SS(CH$_2$)$_q$NS and the like, and esters, such as —CH$_2$—C(=O)—(CH$_2$)$_p$C(=O)O(CH$_2$)$_q$NSC and the like, wherein p and q are integers from about 1 to about 8.

Examples of chelating agents include:
1,4,7,10-tetraazacyclododecane-N-(Gly$_3$(p-NCS-Phe-amide)acetyl)-N',N",N'"-triacetic acid;
1,4,7,10-tetraazacyclotridecane-N-(Gly$_3$(p-NCS-Phe-amide)acetyl)-N',N",N'"-triacetic acid;
1,4,8,11-tetraazacyclotetradecane-N-(Gly$_3$(p-NCS-Phe-amide)acetyl)-N',N",N'"-triacetic acid;
1,5,9,13-tetraazacyclohexadecane-N-(Gly$_3$(p-NCS-Phe-amide)acetyl)-N',N",N'"-triacetic acid;
ethylenediamine-N-(Gly$_3$(p-NCS-Phe-amide)acetyl) triacetic acid;
diethylenetriamine-N-(Gly$_3$(p-NCS-Phe-amide)acetyl)-N'-acetamide-N",N'",N""-triacetic acid;
1,4,7,10-tetraazacyclododecane-N-(Gly$_2$(p-NCS-Phe-amide)acetyl)-N',N",N'"-triacetic acid;
1,4,7,10-tetraazacyclododecane-N-(Gly$_4$(p-NCS-Phe-amide)acetyl)-N',N",N'"-triacetic acid;
1,4,7,10-tetraazacyclododecane-N-(Gly$_5$(p-NCS-Phe-amide)acetyl)-N',N",N'"-triacetic acid;
1,4,7,10-tetraazacyclododecane-N-(Gly$_6$(p-NCS-Phe-amide)acetyl)-N',N",N'"-triacetic acid;
1,4,7,10-tetraazacyclododecane-N,N'-di(Gly$_3$(p-NCS-Phe-amide)acetyl)-N",N'"-diacetic acid;
1,4,7,10-tetraazacyclotridecane-N,N'-di(Gly$_3$(p-NCS-Phe-amide)acetyl)-N",N'"-diacetic acid;
1,4,8,11-tetraazacyclotetradecane-N,N'-di(Gly$_3$(p-NCS-Phe-amide)acetyl)-N",N'"-diacetic acid;
1,5,9,13-tetraazacyclohexadecane-N,N'-di(Gly$_3$(p-NCS-Phe-amide)acetyl)-N",N'"-diacetic acid;
ethylenediamine-N,N'-di(Gly$_3$(p-NCS-Phe-amide)acetyl)-N",N'"-diacetic acid;
diethylenetriamine-N,N'-di(Gly$_3$(p-NCS-Phe-amide)acetyl)-N'"-acetamide-N"",N""'-diacetic acid;
1,4,7,10-tetraazacyclododecane-N-(Gly$_3$(p-NCS-Phe-amide)acetyl)-N'-acetamide-N",N'"-diacetic acid;
1,4,7,10-tetraazacyclotridecane-N-(Gly$_3$(p-NCS-Phe-amide)acetyl)-N'-acetamide-,N",N'"-diacetic acid;
1,4,8,11-tetraazacyclotetradecane-N-(Gly$_3$(p-NCS-Phe-amide)acetyl)-N'-acetamide-N",N'"-diacetic acid;
1,5,9,13-tetraazacyclohexadecane-N-(Gly$_3$(p-NCS-Phe-amide)acetyl)-N'-acetamide-N",N'"-diacetic acid;
ethylenediamine-N-(Gly$_3$(p-NCS-Phe-amide)acetyl)-N'-acetamide-N",N'"-diacetic acid;
diethylenetriamine-N-(Gly$_3$(p-NCS-Phe-amide)acetyl)-N',N"-diacetamide-N'",N""-diacetic acid;
1,4,7,10-tetraazacyclododecane-N-(Gly$_3$(p-SH-Phe-amide)acetyl)-N',N",N'"-triacetic acid;
1,4,7,10-tetraazacyclododecane-N-(Gly$_3$(p-succinimidyl ester-Phe-amide)acetyl)-N',N",N'"-triacetic acid;
1,4,7,10-tetraazacyclododecane-N-(Gly$_3$(p-chloroformyl-Phe-amide)acetyl)-N',N",N'"-triacetic acid; and
1,4,7,10-tetraazacyclododecane-N-(Gly$_3$(p-chloroacetyl-Phe-amide)acetyl)-N',N",N'"-triacetic acid.

Examples of radiolabeled chelates include:
$^{90}$Y$^{III}$-1,4,7,10-tetraazacyclododecane-N-(Gly$_3$(p-NCS-Phe-amide)acetyl)-N',N",N'"-triacetate;
$^{90}$Y$^{III}$-1,4,7,10-tetraazacyclotridecane-N-(Gly$_3$(p-NCS-Phe-amide)acetyl)-N',N",N'"-triacetate;
$^{90}$Y$^{III}$-1,4,8,11-tetraazacyclotetradecane-N-(Gly$_3$(p-NCS-Phe-amide)acetyl)-N', N",N'"-triacetate;
$^{90}$Y$^{III}$-1,5,9,13-tetraazacyclohexadecane-N-(Gly$_3$(p-NCS-Phe-amide)acetyl)-N', N",N'"-triacetate;
$^{90}$Y$^{III}$-ethylenediamine-N-(Gly$_3$(p-NCS-Phe-amide)acetyl) triacetate;
$^{90}$Y$^{III}$-diethylenetriamine-N-(Gly$_3$(p-NCS-Phe-amide)acetyl)-N'-acetamide-N",N'",N""-triacetate;
$^{111}$In$^{III}$-1,4,7,10-tetraazacyclododecane-N-(Gly$_3$(p-NCS-Phe-amide)acetyl)-N',N",N'"-triacetate;
$^{111}$In$^{III}$-1,4,7,10-tetraazacyclotridecane-N-(Gly$_3$(p-NCS-Phe-amide)acetyl)-N',N",N'"-triacetate;
$^{111}$In$^{III}$-1,4,8,11-tetraazacyclotetradecane-N-(Gly$_3$(p-NCS-Phe-amide)acetyl)-N',N",N'"-triacetate;
$^{111}$In$^{III}$-1,5,9,13-tetraazacyclohexadecane-N-(Gly$_3$(p-NCS-Phe-amide)acetyl)-N',N",N'"-triacetate;
$^{111}$In$^{III}$-ethylenediamine-N-(Gly$_3$(p-NCS-Phe-amide)acetyl)triacetate;
$^{111}$In$^{III}$-diethylenetriamine-N-(Gly$_3$(p-NCS-Phe-amide)acetyl)-N'-acetamide-N",N'",N""-triacetate;
$^{67}$Cu$^{II}$-1,4,7,10-tetraazacyclododecane-N,N'-di(Gly$_3$(p-NCS-Phe-amide)acetyl)-N",N'"-diacetate;
$^{67}$Cu$^{II}$-1,4,7,10-tetraazacyclotridecane-N,N'-di(Gly$_3$(p-NCS-Phe-amide)acetyl)-N",N'"-diacetate;

$^{67}Cu^{II}$-1,4,8,11-tetraazacyclotetradecane-N,N'-di(Gly$_3$(p-NCS-Phe-amide)acetyl)-N",N'''-diacetate;

$^{67}Cu^{II}$-1,5,9,13-tetraazacyclohexadecane-N,N'-di(Gly$_3$(p-NCS-Phe-amide)acetyl)-N",N'''-diacetate;

$^{67}Cu^{II}$-ethylenediamine-N,N'-di(Gly$_3$(p-NCS-Phe-amide) acetyl)-N",N'''-diacetate;

$^{67}Cu^{II}$-diethylenetriamine-N,N'-di(Gly$_3$(p-NCS-Phe-amide) acetyl)-N"-acetamide-N''',N''''-diacetate;

$^{67}Cu^{II}$-1,4,7,10-tetraazacyclododecane-N-(Gly$_3$(p-NCS-Phe-amide)acetyl)-N'-acetamide-N",N'''-diacetate;

$^{67}Cu^{II}$-1,4,7,10-tetraazacyclotridecane-N-(Gly$_3$(p-NCS-Phe-amide)acetyl)-N'-acetamide-,N",N'''-diacetate;

$^{67}Cu^{II}$-1,4,8,11-tetraazacyclotetradecane-N-(Gly$_3$(p-NCS-Phe-amide)acetyl)-N'-acetamide-N",N'''-diacetate;

$^{67}Cu^{II}$-1,5,9,13-tetraazacyclohexadecane-N-(Gly$_3$(p-NCS-Phe-amide)acetyl)-N'-acetamide-N",N'''-diacetate;

$^{67}Cu^{II}$-ethylenediamine-N-(Gly$_3$(p-NCS-Phe-amide) acetyl)-N'-acetamide-N",N'''-diacetate; and $^{67}Cu^{II}$-diethylenetriamine-N-(Gly$_3$(p-NCS-Phe-amide) acetyl)-N',N"-diacetamide-N''',N''''-diacetate.

C. Purification of the Radiolabeled Chelate

The second step of prelabeling involves purification of the radiolabeled chelate. The aqueous chelating agent-radionuclide reaction mixture obtained in the first step of prelabeling may be purified by preparing an appropriate anion exchange medium, eluting the aqueous mixture through the medium, and collecting the eluent. Methods for preparing and using anion exchange media are well established and known to those skilled in the art. If necessary or desired, the eluent may be further concentrated by known methods.

The use of the well established technique of anion exchange chromatography to purify the radiolabeled chelate offers a number of practical advantages over other known methods of purification.

For example, the aqueous reaction mixture obtained in the first step of prelabeling may be purified simply and quickly by anion exchange chromatography to provide the purified compound in aqueous solution and in the absence of organic solvents. Consequently, there is no need to remove organic solvents from the purified material before proceeding with formation of the radiolabeled-chelating agent-ligand complex, as required by the existing prelabeling methods [see, for example, Linder et al., 1991; Schlom et al., 1991, supra]. The anion exchange chromatography purification step of the present invention saves time and thereby reduces the loss of radioactive potency and minimizes autoradiolysis.

Purification of the chelate by anion exchange chromatography can be significantly improved by selecting chelating agents and radionuclides with equal and opposite electrical charges. The resulting radiolabeled chelate is electrically neutral. The other important species in the chelation reaction mixture, such as excess chelating agent, complexes containing differently charged metal ions, and quenching agent complexes, are negatively charged. Thus, the electrically neutral radiolabeled chelate of interest can be filtered quickly through an appropriately designed anion-exchange column in H$_2$O to separate them from anionic species. Purification can be further improved by selecting chelating agent/radionuclide charges of −3/+3, so that chelates formed from adventitious cations, such as Ca$^{+2}$ and Mg$^{+2}$ are anionic.

Any appropriately prepared anion exchange material may be used to effect purification of the radiolabeled chelate. Commercially available (Sigma Chemical Company) anion exchange media include, for example, dextran-based anion exchange media such as DEAE Sephadex and QAE Sephadex, agarose-based anion exchange media such as DEAE Sepharose and Q Sepharose, cellulose-based anion exchange media, such as DEAE Sephacel, DEAE Cellulose, ECTEOLA Cellulose, PEI Cellulose, QAE Cellulose, and polystyrene-based anion exchange media, such as Amberlite and Dowex. Criteria for choosing and methods of preparation of anion exchange media are well established and known to those of skill in the art. At present, the preferred anion exchange medium is DEAE Cellulose prepared in acetate form.

D. Formation of the Complex

The third step of prelabeling, conjugation, involves the formation of a radiolabeled-chelating agent-ligand complex (denoted herein variously as the chelate-ligand complex or the complex).

The term "ligand", as used herein, relates to compounds which may perform the role of targeting molecules, including, for example, targeting biomolecules such as antibodies, serum proteins, cell surface receptors, and tumor-specific targeting agents, such as bleomycin. The term "antibody" as used herein is generic to polyclonal antibodies, monoclonal antibodies, chimeric antibodies, antibody fragments (particularly antibody binding fragments), recombinant single chain antibody fragments, and the like. Methods for the preparation of appropriate ligands, such as mAbs, are well established and known to those of skill in the art [See, for example, Fell et al., 1992, supra].

Reaction conditions useful for the formation of the complex from the radiolabeled chelate and ligand, such as pH, temperature, salt concentration, and the like, will reflect the reactive pair of functional groups involved. In particular, reaction conditions useful for the formation of conjugates via functional groups present on proteins are well established and known to those of skill in the art. Typically, aqueous solutions or suspensions of the radiolabeled chelate and the ligand are mixed. The pH may be adjusted to optimize conditions for conjugation. For example, for reaction of the amino (—NH$_2$) group of a protein (for example, a mAb) with an isothiocyanato (—NCS) group, the pH may be adjusted to about 8 to 11, more preferably about 9.5, using, for example, a buffer such as aqueous triethylamine. Furthermore, the temperature of the reaction mixture may be adjusted, for example, to 37° C. for 1 hr, to accelerate conjugation. The reaction (incubation) time may be varied to optimize conjugation. Longer reaction times would lead to higher conjugation yields; however, for radioactivity levels appropriate for clinical use (≈100 millicuries, mCi), radiolysis will become important at longer times.

In the conjugation step, a high concentration of ligand (for example, mAb) is desired, so that each reactive functional group present on the radiolabeled-chelate (for example, isothiocyanate groups) will frequently encounter reactive functional groups on the ligand (for example, amino groups) with which to react. It may be desirable to concentrate the radiolabeled chelate prior to the conjugation step to avoid dilution of the conjugation mixture, particularly when small amounts of radioactivity are used. Optimally, ligand concentrations as high as are practical are desired, for example, about 10 to 500 mg/mL (the reaction mixture concentration of the chimeric mAb 16 ligand of Example 3 was about 20 mg/mL).

After conjugation, the complex may be separated from the reaction mixture and purified using known methods, for example, using a centrifuged gel-filtration column [Penefsky et al., 1979, *Methods Enzymol.*, 56, Part G:527–530; Meares et al., 1984, *Anal. Biochem.*, 142:68–78].

E. Use

One application of the radionuclide-labeled chelating agent-ligand complexes of the invention is for use in radioimaging. A variety of metal chelates, when conjugated with serum proteins, target-specific antibodies, or bleomycin can be localized in tumor or other target tissue to provide useful radioimaging images used in localizing tumors [Meares et al., 1984; Goodwin et al., 1979, *Radiopharmaceuticals II, Proceedings of the Second International Symposium on Radiopharmaceuticals* (V. J. Sodd, ed), New York, pp.275–284; De Reimer et al., *J. Lab. Comps. and Radiopharm.*, 18(10):1517; Meares et al., 1976, Proc. Natl. Acad. Sci. U.S.A., 73(11):3803; Leung et al., 1978, Int. J. Appl. Rad. Isot., 29:687; Goodwin et al., 1981, *J. Nucl. Med.*, 22(9):787]. For example, a composition comprising the radionuclide-labelled chelating agent-ligand complex and a pharmaceutically acceptable carrier is injected in a patient and allowed to localize, for example, in a tumor region(s). These regions are imaged using radioimaging equipment such as γ photon emission tomograph or a position emission computed tomograph. Various stratagems may be used to enhance the image contrast which is achievable. For example, with a complex formed with a serum protein, the image contrast can be improved by administering an anti-complex antibody following tumor uptake of the complex, to increase the rate of clearance of the complex from the bloodstream [Goodwin et al., 1981, supra].

The radionuclide-labeled chelating agent-ligand complexes of the invention are also suitable for use as therapeutic agents based, for example, on the radiotherapeutic action of the radionuclide when localized in tumor tissue. Again, a composition comprising the radionuclide-labelled chelating agent-ligand complex and a pharmaceutically acceptable carrier is injected in a patient and allowed to localize, for example, in a tumor region(s).

F. Examples

The following examples further illustrate the invention. These examples are not intended to limit the invention in any manner.

Example 1

Preparation of the $^{90}$Y-Labeled Chelating Agent (2)

The prelabeling procedure is shown in FIG. 1. (Bold letters in parentheses refer to the compounds shown in the figures). The bifunctional chelating agent (1) (denoted herein variously as DOTA-Gly$_3$-L-(p-isothiocyanato)-Phe-amide and 1,4,7,10-tetraazacyclododecane-N-(Gly$_3$(L-p-NCS-Phe-amide)acetyl)-N',N'',N'''-triacetic acid) was prepared by the method described by Li et al., 1993, Bioconjugate Chem., 4:275–283. Carrier-free $^{90}$Y (DuPont NEN) in 0.05 M HCl was dried in a heating block under N$_2$(g), and 100 μL of 20 mM (1) in 0.2 M (CH$_3$)$_4$N$^+$ acetate, pH 5.0, was added. The mixture was incubated at 37° C. for 30 min, followed by the addition of 25 μL of 50 Mm DTPA in 0.1 M (CH$_3$)$_4$N$^+$ acetate, pH 6.0, for 15 min at room temperature (quenching; to complex any remaining free yttrium).

An anion-exchange column was prepared by filling a disposable 1 mL tuberculin syringe with 500 μL of DEAE (diethylaminoethyl) Cellulose anion-exchange resin (1 milliequivalent per dry gram; Sigma Chemical Company) and pre-spun for 3 min at ≈2000 g. The resin was converted to acetate form prior to use.

The solution was loaded onto the anion-exchange column, and the column was spun for 2 min at ≈2000 g. followed by elution with four 125 μL aliquots of H$_2$O by centrifugation at ≈2000 g for 2 min each. Most of the radioactive compound (2) (denoted herein variously as $^{90}$Y$^{III}$-DOTA-Gly$_3$-L-(p-isothiocyanato)-Phe-amide and $^{90}$Y$^{III}$-1,4,7,10-tetraazacyclododecane-N-(Gly$_3$(L-p-NCS-Phe-amide) acetyl)-N',N'',N'''-triacetate) was recovered in the first four fractions (see Table 1). One-step elution with 0.5 mL of H$_2$O was performed for comparison, but it gave 18% lower recovery than stepwise elution with 0.5 mL of H$_2$O was performed for comparison, but it gave 18% lower recovery then stepwise elution.

All the eluted fractions were collected and concentrated to ≈15 μL with a speed-vac concentrator (Savant Instruments) without heating. It should be possible to avoid this step when larger amounts of radioactivity are used.

In the chelation step, the yield after anion-exchange was typically >70% of the starting radioactivity. Particularly for $^{90}$Y solutions, the levels of metal impurities appear to vary with each batch of carrier-free radiometal. The identity of these impurities is difficult to determine, but most common metal contaminants are divalent ions. Pre-labeling deals with the impurity problem by using a large excess of chelating agent, and then removing the excess. This is preferable to using a large excess of chelate-tagged mAb conjugate, which cannot be fractionated later to remove unwanted contaminants. Obviously, pre-labeling does not eliminate trivalent metal complexes from the product.

Example 2

Preparation of the $^{111}$In-Labeled Chelating Agent (2)

$^{111}$In-labeled chelate (2) was prepared by the general procedure of Example 1.

Example 3

Preparation of the Radionuclide-Labeled Chelating Agent-Targeting Molecule Complex (3)

Concentrated solutions of the labeled chelating agent of Example 1 (and alternatively of Example 2) were mixed with 1 mg of chimeric mAb 16 (18 μL, 56 mg/mL; Oncogen/Bristol-Myers) [Fell et al., 1992, *J. Biol. Chem.*, 267:15552–15558] in 0.1 M (CH$_3$)$_4$N$^+$ phosphate, pH 9.0. The pH was adjusted to 9.5 using aqueous 2.0 M triethylamine. The mixture was incubated at 37° C. for 1 hr and compound (3) was isolated using a centrifuged gel-filtration column [Penefsky et al., 1979; Meares et al. 1984, supra]. Yields are listed in Table 1.

TABLE 1

Results for DOTA-Peptide Radiolabeling and Conjugation

| Radionuclide | Starting Radioactivity (volume) | Recovery for Step 2† (radiolabeling) | Recovery for Step 3† (conjugation) | Overall Recovery† |
|---|---|---|---|---|
| $^{90}$Y | 2.1–3.9 mCi (2–5 μL) | 80% ± 5% | 40% ± 2% | 30% ± 4% |
| $^{111}$In | 4.9–6.2 mCi (12–30 μL) | 70% ± 9% | 73 ± 3% | 42% ± 4% |

†Average recovered radioactivity ± standard deviation, for ≧3 runs.

The radiochemical purity of both $^{90}$Y-and $^{111}$In-labeled immunoconjugates (3) was determined to be >95% by gel filtration HPLC cellulose acetate electrophoresis, and silica gel TLC [Meares et al., 1984, supra]. A solid-phase radioimmunoassay [DeNardo et al., 1986, *Nucl. Med. Biol.*, 13:303–310] was performed using $^{125}$I-labeled chimeric L6 as a standard. The immunoreactivity of $^{90}$Y-DOTA-Gly$_3$-L-Phe-amide-thiourea-chimeric L6 was 107±5% relative to $^{125}$I-labeled antibody.

Example 4

Figure 2:
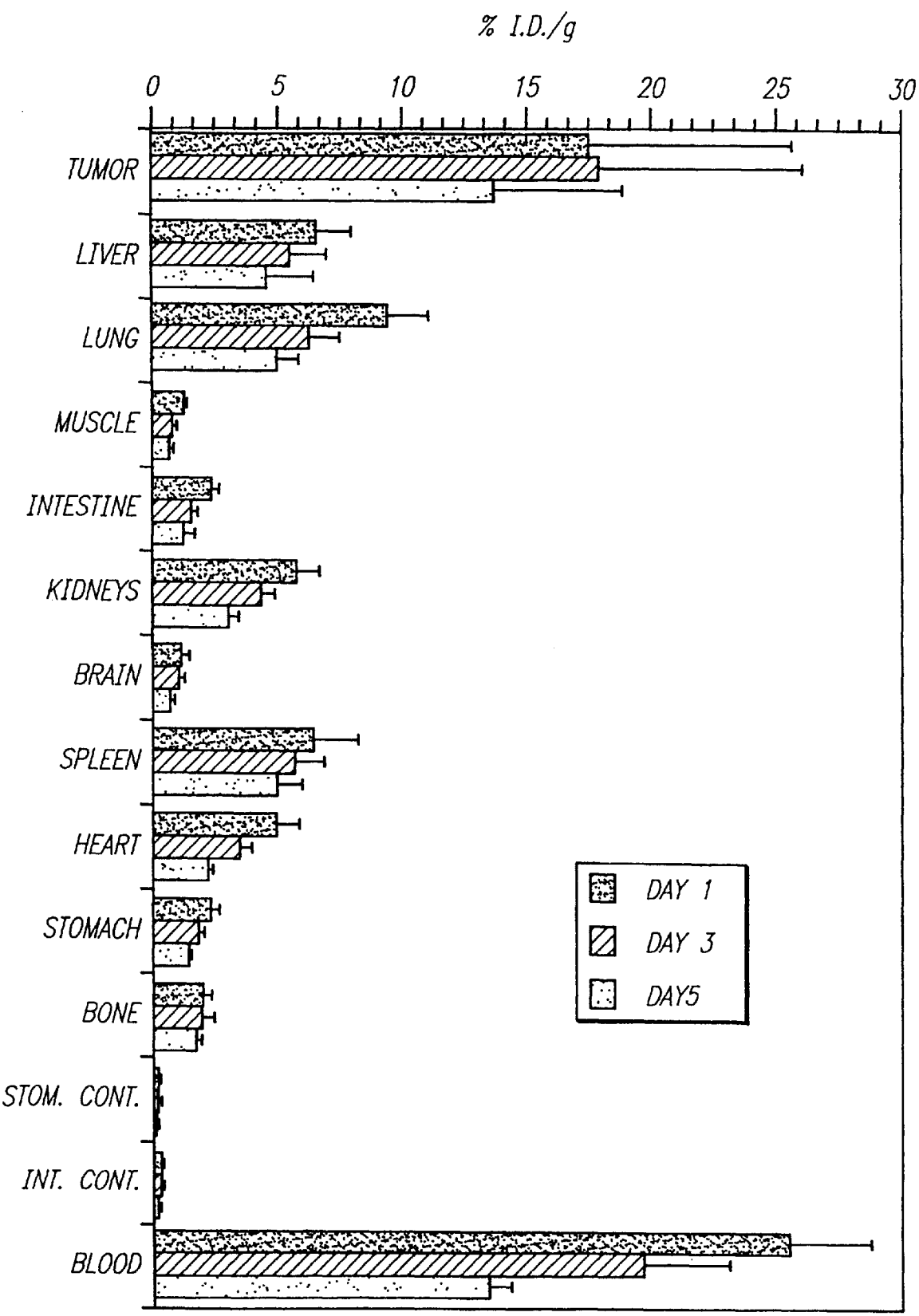
FIG. 2 is a graph depicting the biodistribution of $^{90}$Y-DOTA-Gly$_3$-L-Phe-amide-thiourea-chimeric mAb L6 (compound (3) of FIG. 1) in HBT tumor-bearing nude mice at day 1, day 3, and day 5. For each time point, data were acquired from 7 animals. The values are given as average percent of injected dose per gram of tissue. Error bars represent 1 standard deviation.

Biodistribution of the Radionuclide-Labeled Chelating Agent-Targeting Molecule Complex To examine the properties of the conjugate in vivo, $^{90}$Y-labeled compound (3) was injected into HBT tumor-bearing nude mice [Hellström et al., 1986, *Cancer Res.*, 46:3917–3923] for organ distribution and tumor uptake studies. The results of these animal studies (summarized in FIG. 2) showed that the radioactivity level in the liver varied from 6.4±1.5% I.D./g on the first day to 5.4±1.5% I.D./g on the third day to 4.6±1.9% I.D./g on the fifth day. The units I.D./g indicate percent of injected dose per gram of tissue. The tumor uptake was 17.5±8.0% I.D./g on day 1, 18.0±8.0% I.D./g on day 3 and 13.8%±5.2% I.D./g on day 5. The bone uptake was 2.1±0.3% I.D./g, 2.0±0.5% I.D./g, and 1.8±0.2% I.D./g on days 1, 3, and 5. The levels of radioactivity in liver and bone are satisfactorily low [Deshpande et al., 1990, supra], and the tumor uptake is good.

All publications, patents, and patent applications cited in this specification are herein incorporated by reference as if each individual publication, patent, or patent application were specifically and individually indicated to be incorporated by reference.

We claim:

1. A method for preparing a radionuclide-labeled chelating agent-ligand complex comprising:
   (a) reacting an anionic chelating agent with excess cationic radionuclide in aqueous solution to form:
      (i) an electrically non-negative radionuclide chelate in aqueous solution; and,
      (ii) remaining free cationic radionuclide in aqueous solution,
   wherein said anionic chelating agent has a chelating group and at least one pendant linker group that is capable of covalently binding a ligand;
   (b) reacting an anionic quenching agent in aqueous solution with the remaining free cationic radionuclide of the aqueous reaction mixture of step (a) to form an anionic radionuclide-quenching agent chelate in aqueous solution;
   (c) purifying said electrically non-negative radionuclide chelate from the aqueous reaction mixture of step (b), and away from said anionic radionuclide-quenching agent chelate, wherein said purifying step consists essentially of filtering said reaction mixture through an anion exchange medium, whereby said anionic radionuclide-quenching agent chelate is bound and retained by said anion exchange medium while said electrically non-negative radionuclide chelate passes through said anion exchange medium, to yield purified electrically non-negative radionuclide chelate in aqueous solution; and
   (d) reacting said purified electrically non-negative radionuclide chelate of step (c) with said ligand in aqueous solution to form said complex in aqueous solution, wherein said at least one pendant linker group is covalently bound to said ligand.

2. The method of claim 1 wherein the electrical charge of said radionuclide is +2 and the electrical charge of said chelating agent is −2.

3. The method of claim 1 wherein the electrical charge of said radionuclide is +3 and the electrical charge of said chelating agent is −3.

4. The method of claim 1 wherein said radionuclide is $^{90}$Y or $^{111}$In.

5. The method of claim 1 wherein said chelating group is a macrocyclic group.

6. The method of claim 1 wherein said chelating group is a polyazamacrocyclic group or a polyoxamacrocyclic group.

7. The method of claim 1 wherein said chelating group is derived from
   1,4,7,10-tetraazacyclododecane-N,N',N'',N'''-tetraacetic acid;
   1,4,7,10-tetraazacyclotridecane-N,N',N'',N'''-tetraacetic acid;
   1,4,8,11-tetraazacyclotetradecane-N,N',N'',N'''-tetraacetic acid; or
   1,5,9,13-tetraazacyclohexadecane-N,N',N'',N'''-tetraacetic acid.

8. The method of claim 1 wherein said chelating agent is N-substituted 1,4,7,10-tetraazacyclododecane-N,N',N'',N'''-tetraacetic acid wherein said N-substituent is —CH$_2$C(=O)-(Gly)$_3$-L-(p-isothiocyanato)-Phe-amide and said radionuclide is $^{90}$Y or $^{111}$In.

9. The method of claim 1 wherein said ligand is an antibody.

10. The method of claim 1 wherein said ligand is a monoclonal antibody.

11. The method of claim 4 wherein said ligand is an antibody.

12. The method of claim 4 wherein said ligand is a monoclonal antibody.

13. The method of claim 8 wherein said ligand is an antibody.

14. The method of claim 8 wherein said ligand is a monoclonal antibody.

* * * * *

UNITED STATES PATENT AND TRADEMARK OFFICE
CERTIFICATE OF CORRECTION

PATENT NO. : 5,958,374
DATED : September 28, 1999
INVENTOR(S) : Claude F. MEARES *et al.*

It is certified that error appears in the above-identified patent and that said Letters Patent is hereby corrected as shown below:

In column 12, line 38, please replace "(p-isothiocyanato)" with --(*p*-isothiocyanato)--.

Signed and Sealed this

Fifteenth Day of August, 2000

Q. TODD DICKINSON

Attest:

*Attesting Officer*  *Director of Patents and Trademarks*